US00RE48555E

(19) United States
(12) Reissued Patent
Cancio et al.

(10) Patent Number: US RE48,555 E
(45) Date of Reissued Patent: *May 18, 2021

(54) BREATHABLE AND MICROPOROUS THIN THERMOPLASTIC FILM

(71) Applicant: CLOPAY PLASTIC PRODUCTS COMPANY, INC., Mason, OH (US)

(72) Inventors: Leopoldo V. Cancio, Vero Beach, FL (US); Frank Eschenbacher, Schnelldorf (DE); Jerry Ford, Maineville, OH (US)

(73) Assignee: Berry Film Products Company, Inc., Evansville, IN (US)

( * ) Notice: This patent is subject to a terminal disclaimer.

(21) Appl. No.: 15/700,282

(22) Filed: Sep. 11, 2017

Related U.S. Patent Documents

Reissue of:
(64) Patent No.: 9,492,332
Issued: Nov. 15, 2016
Appl. No.: 14/709,728
Filed: May 12, 2015

U.S. Applications:
(60) Provisional application No. 62/092,351, filed on Dec. 16, 2014, provisional application No. 62/053,385,
(Continued)

(51) Int. Cl.
*A61F 13/15* (2006.01)
*B29C 48/08* (2019.01)
(Continued)

(52) U.S. Cl.
CPC .. *A61F 13/15707* (2013.01); *A61F 13/15699* (2013.01); *A61F 13/51401* (2013.01);
(Continued)

(58) Field of Classification Search
CPC ..... B29C 48/08; A61F 13/51478; A61F 13/51462; B32B 27/12; B32B 27/205; C08J 5/18
See application file for complete search history.

(56) References Cited

U.S. PATENT DOCUMENTS 3,520,964 A 7/1970 Metz, Jr.
3,796,785 A 3/1974 Rest
(Continued)

FOREIGN PATENT DOCUMENTS

CA 2802583 A1 12/2010
CN 100430221 C 11/2004
(Continued)

OTHER PUBLICATIONS

Indonesian Office Action for Indonesian Patent App. No. P-00201607612, 5 pages.
(Continued)

*Primary Examiner* — Carlos Lopez
(74) *Attorney, Agent, or Firm* — Barnes & Thornburg LLP

(57) ABSTRACT

Breathable, thermoplastic films, laminates, and methods of making films having a basis weight less than or equal to 15 gsm and a water vapor transmission rate of at least about 500 grams $H_2O$/24-hour/$m^2$, wherein the film has a ratio of the MD load at break to the CD load at break of less than about 10, and at least one of a machine-direction notched Elmendorf tear strength of at least about 5 g or a machine-direction notched trapezoidal tear strength of at least about 15 g.

20 Claims, 1 Drawing Sheet

Related U.S. Application Data filed on Sep. 22, 2014, provisional application No. 61/992,438, filed on May 13, 2014.

(51) Int. Cl.

| | |
|---|---|
| ***A61F 13/514*** | (2006.01) |
| ***B32B 27/12*** | (2006.01) |
| ***B32B 27/20*** | (2006.01) |
| ***B32B 27/32*** | (2006.01) |
| ***C08J 5/18*** | (2006.01) |
| *B29K 23/00* | (2006.01) |
| *B29K 101/12* | (2006.01) |
| *B29L 7/00* | (2006.01) |

(52) U.S. Cl.

CPC .. *A61F 13/51462* (2013.01); *A61F 13/51478* (2013.01); *B29C 48/08* (2019.02); *B32B 27/12* (2013.01); *B32B 27/20* (2013.01); *B32B 27/205* (2013.01); *B32B 27/32* (2013.01); *C08J 5/18* (2013.01); *A61F 2013/15292* (2013.01); *A61F 2013/15406* (2013.01); *A61F 2013/15544* (2013.01); *A61F 2013/15715* (2013.01); *A61F 2013/51431* (2013.01); *B29K 2023/04* (2013.01); *B29K 2023/10* (2013.01); *B29K 2101/12* (2013.01); *B29L 2007/008* (2013.01); *B32B 2264/104* (2013.01); *B32B 2270/00* (2013.01); *B32B 2305/026* (2013.01); *B32B 2307/514* (2013.01); *B32B 2555/00* (2013.01); *B32B 2555/02* (2013.01); *C08J 2323/06* (2013.01); *C08J 2323/08* (2013.01); *C08J 2323/12* (2013.01); *C08J 2423/12* (2013.01); *Y10T 428/27* (2015.01)

(56) References Cited

U.S. PATENT DOCUMENTS

| | | | |
|---|---|---|---|
| 3,816,886 | A | 6/1974 | Van Cappellen |
| 4,066,729 | A | 1/1978 | Van Cappellen |
| 4,275,105 | A | 6/1981 | Boyd et al. |
| 4,310,485 | A | 1/1982 | Dauber |
| 4,436,888 | A | 3/1984 | Copple |
| 4,632,869 | A | 12/1986 | Park |
| 4,636,869 | A | 1/1987 | Tomohisa |
| 4,668,463 | A | 5/1987 | Cancio et al. |
| 4,704,238 | A | 11/1987 | Okuyama |
| 4,758,462 | A | 7/1988 | Park |
| 4,874,567 | A | 10/1989 | Lopatin |
| 4,929,303 | A | 5/1990 | Sheth |
| 5,028,289 | A | 7/1991 | Rasmussen |
| 5,192,606 | A | 3/1993 | Proxmire et al. |
| 5,236,963 | A | 8/1993 | Jacoby et al. |
| 5,261,899 | A | 11/1993 | Visscher et al. |
| 5,382,461 | A | 1/1995 | Wu |
| 5,422,172 | A | 6/1995 | Wu |
| 5,445,862 | A | 8/1995 | Kaneko et al. |
| 5,558,930 | A | 9/1996 | Dipoto |
| 5,560,974 | A | 10/1996 | Langley |
| 5,709,932 | A | 1/1998 | Glez et al. |
| 5,814,178 | A | 9/1998 | Jacobs |
| 6,045,900 | A | 4/2000 | Haffner |
| 6,075,179 | A | 6/2000 | McCormack et al. |
| 6,156,421 | A | 12/2000 | Stopper |
| 6,245,271 | B1 | 6/2001 | Jacobs et al. |
| 6,258,308 | B1 | 7/2001 | Brady et al. |
| 6,309,736 | B1 | 10/2001 | McCormack et al. |
| 6,375,781 | B1 | 4/2002 | Wojcik et al. |
| 6,509,513 | B2 | 1/2003 | Glaug et al. |
| 6,575,726 | B1 | 6/2003 | Nissel |
| 6,638,636 | B2 | 10/2003 | Tucker |
| 6,653,523 | B1 | 11/2003 | McCormack et al. |
| 6,676,871 | B1 | 1/2004 | Benassi et al. |
| 6,811,643 | B2 | 11/2004 | McAmish et al. |
| 6,818,083 | B2 | 11/2004 | McAmish et al. |
| 6,909,028 | B1 | 6/2005 | Shawver et al. |
| 6,953,510 | B1 | 10/2005 | Mackay et al. |
| 6,991,758 | B2 | 1/2006 | Krumm et al. |
| 7,270,723 | B2 | 9/2007 | McCormack et al. |
| 7,307,031 | B2 | 12/2007 | Carroll et al. |
| 7,442,332 | B2 | 10/2008 | Cancio et al. |
| 7,501,363 | B2 | 3/2009 | Dharmadhikary et al. |
| 7,510,758 | B2 | 3/2009 | Thomas et al. |
| 7,629,042 | B2 | 12/2009 | Jones et al. |
| 7,776,771 | B2 | 8/2010 | Autran et al. |
| 7,833,211 | B2 | 11/2010 | Mansfield |
| 7,879,452 | B2 | 2/2011 | Muslet |
| 7,932,196 | B2 | 4/2011 | McCormack et al. |
| 8,067,501 | B2 | 11/2011 | Fiscus et al. |
| 8,092,731 | B2 | 1/2012 | Guenanten et al. |
| 8,163,216 | B2 | 4/2012 | Bormann et al. |
| 8,298,630 | B2 | 10/2012 | Nitta et al. |
| 8,383,246 | B2 | 2/2013 | Frauenhofer et al. |
| 8,445,744 | B2 | 5/2013 | Autran et al. |
| 8,865,294 | B2 | 10/2014 | Cisek |
| 8,937,211 | B2 | 1/2015 | Dent et al. |
| 9,169,366 | B2 | 10/2015 | Weisman |
| 9,573,729 | B2 | 2/2017 | Cobler |
| D811,897 | S | 3/2018 | Cisek |
| D811,898 | S | 3/2018 | Pszczolkowski |
| D811,899 | S | 3/2018 | Kuhl |
| D813,054 | S | 3/2018 | Pszczolkowski |
| D817,779 | S | 5/2018 | Pszczolkowski |
| D842,706 | S | 3/2019 | Pszczolkowski |
| 2002/0074691 | A1 | 6/2002 | Mortellite |
| 2002/0187361 | A1 | 12/2002 | Amon |
| 2003/0039851 | A1 | 2/2003 | Hale |
| 2003/0045844 | A1 | 3/2003 | Taylor et al. |
| 2003/0077471 | A1 | 4/2003 | Tucker |
| 2003/0161995 | A1 | 8/2003 | Kauschke et al. |
| 2004/0015142 | A1 | 1/2004 | Johnston et al. |
| 2004/0122398 | A1 | 6/2004 | Schnabel et al. |
| 2004/0157333 | A1 | 8/2004 | McAmish |
| 2005/0042962 | A1 | 2/2005 | McCormack et al. |
| 2005/0110713 | A1 | 5/2005 | Chung |
| 2005/0248051 | A1* | 11/2005 | Cancio ..... B29C 55/06 264/154 |
| 2006/0147716 | A1 | 7/2006 | Braverman |
| 2006/0148361 | A1 | 7/2006 | Ng |
| 2006/0269710 | A1 | 11/2006 | Inglis |
| 2008/0147034 | A1 | 6/2008 | Wang et al. |
| 2008/0233375 | A1 | 9/2008 | Wright |
| 2010/0040875 | A1 | 2/2010 | Patel |
| 2010/0076390 | A1 | 3/2010 | Norrby |
| 2010/0216963 | A1 | 8/2010 | Ueda |
| 2011/0052105 | A1 | 3/2011 | Wilcoxen |
| 2011/0218316 | A1 | 9/2011 | Drysdale |
| 2011/0282313 | A1 | 11/2011 | Lu et al. |
| 2012/0033900 | A1 | 2/2012 | Fraser |
| 2012/0063706 | A1 | 3/2012 | Fraser |
| 2012/0077113 | A1 | 3/2012 | Kim et al. |
| 2012/0217682 | A1 | 8/2012 | Vignola |
| 2012/0237743 | A1 | 9/2012 | O'Donnell |
| 2012/0237746 | A1 | 9/2012 | O'Donnell et al. |
| 2012/0269465 | A1 | 10/2012 | Dorsey |
| 2013/0028542 | A1 | 1/2013 | Borchardt |
| 2013/0041335 | A1 | 2/2013 | Dwiggins et al. |
| 2013/0202853 | A1 | 8/2013 | Bergman |
| 2014/0248484 | A1 | 9/2014 | Bormann et al. |
| 2016/0114071 | A1 | 4/2016 | Topolkaraev |

FOREIGN PATENT DOCUMENTS

| | | | |
|---|---|---|---|
| CN | 1976797 | | 6/2007 |
| CN | 1976797 | A | 6/2007 |
| CN | 1976797 | B | 12/2010 |
| CN | 101959907 | | 1/2011 |
| CN | 102292056 | | 12/2011 |
| CN | 103429430 | A | 12/2013 |
| EP | 0283200 | | 9/1988 |
| EP | 0283200 | A2 | 9/1988 |
| EP | 1423275 | A1 | 6/2004 |
| EP | 1423275 | B1 | 6/2004 |

(56) References Cited

FOREIGN PATENT DOCUMENTS

| | | | |
|---|---|---|---|
| EP | 1250225 | B1 | 8/2005 |
| JP | 04309546 | | 11/1992 |
| JP | H04335043 | | 11/1992 |
| JP | 564080 | A | 3/1994 |
| JP | H07016939 | | 1/1995 |
| JP | H0959408 | | 3/1997 |
| JP | 2003039612 | | 2/2003 |
| JP | 2003526710 | | 9/2003 |
| JP | 2005513960 | A | 5/2005 |
| JP | 2005518290 | | 6/2005 |
| JP | 2005525247 | A | 8/2005 |
| JP | 2006199786 | | 8/2006 |
| JP | 2007045046 | A | 2/2007 |
| JP | 2007503326 | | 2/2007 |
| JP | 2007536110 | | 12/2007 |
| JP | 2011514391 | | 5/2011 |
| KR | 1020070007893 | | 1/2007 |
| WO | 9805501 | | 2/1998 |
| WO | 9805502 | | 2/1998 |
| WO | 9922930 | | 5/1999 |
| WO | 9922930 | A1 | 5/1999 |
| WO | 9933654 | A1 | 7/1999 |
| WO | 00/23509 | | 4/2000 |
| WO | 0023509 | A1 | 4/2000 |
| WO | 0151548 | | 7/2001 |
| WO | 0151548 | A2 | 7/2001 |
| WO | 2001047710 | A1 | 7/2001 |
| WO | 2001058685 | A1 | 8/2001 |
| WO | 03020513 | A1 | 3/2003 |
| WO | 2003035394 | A1 | 5/2003 |
| WO | 03072338 | A1 | 9/2003 |
| WO | 2005021262 | A1 | 3/2005 |
| WO | 2005110713 | A1 | 11/2005 |
| WO | 2007022990 | | 3/2007 |
| WO | 2009/094506 | | 7/2009 |
| WO | 2009094506 | A1 | 7/2009 |
| WO | 2011019504 | | 2/2011 |
| WO | 2014199268 | A1 | 12/2014 |
| WO | 2005/110713 | | 11/2015 |
| WO | 2015175593 | A1 | 11/2015 |

OTHER PUBLICATIONS

Office Action dated Jan. 15, 2019 for U.S. Appl. No. 15/206,072, (pp. 1-13).
Office Action dated May 17, 2019 for U.S. Appl. No. 15/206,072, (pp. 1-12).
Canadian Office Action for Canadian App. No. 3,004,264 dated Apr. 9, 2019, 8 pages.
Japanese Office Action for Japanese App. No. 2018-522690 dated May 26, 2019, 14 pages.
Japanese Office Action for Japanese App. No. 2016-567675 dated Jul. 22, 2019, 11 pages.
Australian Examination Report for Australian App. No. 2015259236 dated Feb. 26, 2019, 3 pages.
Korean Preliminary Rejection for Korean App. No. 10-2016-7034770 dated Jan. 21, 2019, 15 pages.
European Extended Search Report for EP16824959.7 dated Feb. 19, 2019, 8 pages.
Office Action dated Dec. 11, 2018 for U.S. Appl. No. 15/341,103, (pp. 1-21).
Office Action dated Dec. 11, 2018 for U.S. Appl. No. 15/442,867, (pp. 1-8).
Japanese Office Action for Japanese App. No. 2016-567675 dated Nov. 19, 2018, 11 pages.
PCT, International Search Report and Written Opinion issued in corresponding International Patent Application No. PCT/US2015/030463; 15 pages (dated Oct. 2, 2015).
U.S., Non-Final Office Action, U.S. Appl. No. 14/709,728, 17 pages (dated Apr. 22, 2016).
U.S., Notice of Allowance, U.S. Appl. No. 14/709,728, 8 pages (dated Aug. 10, 2016).
CO, English Translation of Office Action, Colombian Patent Application No. NC2016/0004872, 1 page (dated Dec. 24, 2016).
CN, Search Report (with English translation), Chinese Patent Application No. 2015800270287, 4 pages (dated May 26, 2017).
CN, First Office Action (with English translation), Chinese Patent Application No. 2015800270287, 9 pages (dated Jun. 2, 2017).
Admitted Prior Art—Product Data Sheet BR 124 (Clopay).
Windmöller & Hölscher Technical Data Sheet (2013).
Chinese Decision of Rejection for Chinese App. No. 2015800270287 dated Oct. 11, 2018, 4 pages, (no English translation available).
English Translation of Chinese Decision of Rejection for Chinese App. No. 2015800270287 dated Oct. 11, 2018, 6 pages.
CN, Second Office Action of State Intellectual Property Office (with English translation), Chinese Patent Application No. 2015800270287, 9 pages, dated Jan. 30, 2018.
Columbian Office Action for Columbian App. No. NC2018/0000374 dated Sep. 24, 2019, 26 pages.
Notice of Final Rejection for Korean App. No. 10-2016-7034770, 7 pages.
Office Action dated Aug. 23, 2019 for U.S. Appl. No. 15/206,072, (pp. 1-16).
Notice of Opposition for AU2015259236 sent Aug. 27, 2019, 3 pages.
Office Action dated Sep. 10, 2019 for U.S. Appl. No. 15/341,103 (pp. 1-15).
Columbian Office Action for Columbian App. No. NC2018/0000374 dated Nov. 5, 2019, 31 pages.
European Communication pursuant to Art. 94(3) for EP16824959.7 dated Oct. 10, 2019, 4 pages.
Notice of Preliminary Rejection for Korean App. No. 10-2016-7034770, 5 pages.
Office Action dated Jul. 25, 2018 for U.S. Appl. No. 15/341,103, (pp. 1-12).
Extended European Search Report for European Pat. App. No. 18159121.5 dated Jun. 26, 2018, 11 pages.
Communication Pursuant to Article 94(3) EPC for European Patent App. No. 15724480.7 dated Jun. 18, 2018, 6 pages.
Australian First Examination Report for Australian App. No. 2016350820 dated May 24, 2019, 6 pages.
Office Action dated Jun. 5, 2019 for U.S. Appl. No. 15/442,867, 8 pages.
Columbian Office Action for Columbian App. No. NC2018/0000374 dated May 3, 2019, 35 pages.
Korean Office Action for Korean App. No. 10-2018-7015313 dated Jun. 25, 2019, 33 pages.
Office Action dated Feb. 14, 2019 for U.S. Appl. No. 15/431,073, (pp. 1-15).
Office Action dated Feb. 14, 2019 for U.S. App. No. 15/876,483, (p. 1-9).
Korean Final Office Action for Korean App. No. 10-2018-7015313 dated Dec. 23, 2019, 10 pages.
Chinese Patent Office Action for Chinese App. No. 201680077856.6 dated Dec. 4, 2019, 34 pages.
Australian Examination Report for Australian App. No. 2016350820 dated Jan. 8, 2020, 4 pages.
Office Action dated Jan. 8, 2020 fo U.S. Appl. No. 15/431,073, 17 pages.
Office Action dated Feb. 4, 2020 for U.S. Appl. No. 15/442,867 (pp. 1-9).
Brazilian Search Report for Brazilian Patent App. BR112016025367-1 dated Dec. 5, 2019, 9 pages.
Office Action dated Dec. 19, 2019 for U.S. Appl. No. 15/341,103, 17 pages.
Canadian Office Action for Canadian Patent App. No. 3,004,264 dated Nov. 8, 2019, 3 pages.
Australian Examination Report for Australian App. No. 2016293826 dated Mar. 31, 2020, 3 pages.
Office Action dated Apr. 6, 2020, for U.S. Appl. No. 15/206,072, (pp. 1-25).
Columbian Office Action for Columbian App. No. NC2018/0004912 dated Jan. 29, 2020, 30 pages.

(56) References Cited

OTHER PUBLICATIONS

Statement of Grounds & Particulars of Opposition for Australian App. No. 2015259236 sent Nov. 22, 2019, 4 pages.
Evidence in Support of the Opposition for Australian App. No. 2015259236, 505 pages.
Korean Final Office Action for Korean App. No. 10-2018-7015313 dated Mar. 5, 2020, 10 pages.
Japanese Office Action for Japanese App. No. 2018-522690 dated Jan. 30, 2020, 9 pages.
Brazilian Preliminary Examination Report for Brazilian Patent App. No. BR112018008995-8, dated Feb. 28, 2020, 5 pages, (No English Translation available).
Saudi Arabian First Examination Report for Saudi Arabian App. No. 516380252, 8 pages.
Indian First Examination Report for Indian App. No. 201627041571, dated Feb. 20, 2020, 5 pages.
Redacted Declaration of Robert Koplin as part of Evidence in Reply for Opposition of Australian App. No. 2015259236, 84 pages.
Indian Hearing Notice for Indian App. No. 201627041571, dated Sep. 4, 2020, 2 pages.
Indian First Examination Report for Indian Patent App. No. 201817001177 dated Aug. 24, 2020, 9 pages.
Office Action dated Aug. 28, 2020 for U.S. Appl. No. 15/206,072, (pp. 1-26).
Office Action dated Dec. 8, 2020 for U.S. Appl. No. 15/431,073, (pp. 1-19).
Office Action dated Jan. 4, 2021 for U.S. Appl. No. 15/206,072, (pp. 1-30).
Application for Patent Revocation for Korean App. No. 10-2016-7034770 dated Nov. 30, 2020, 209 pages.
Chinese Reexamination Decision for Chinese App. No. 2015800270287 dated May 8, 2020, 7 pages, (no English translation available).
English Translation of Chinese Reexamination Decision for Chinese App. No. 2015800270287 dated May 8, 2020, 8 pages.
Chinese Decision of Reexamination for Chinese App. No. 2015800270287 dated Oct. 12, 2020, 25 pages.
European Communication pursuant to Art. 94(3) for EP16824959.7 dated Nov. 4, 2020, 6 pages.
Decision of Refusal for Japanese App. No. 2018-521194 dated Nov. 4, 2020, 18 pages.
Notice of Decision for Egyption App. No. 1816/2016 13 pages.
Evidence in Reply for Opposition of Australian App. No. 2015259236, 254 pages.
SML, 100% Extrustion Cast Film Lines: Hygiene Film Brochure, Oct. 2013, 28 pages.
SML, Innovation Days Invitation, Nov. 13-15, 2012, 2 pages.
European Examination Report for European App. No. 16862828.7 dated Oct. 21, 2020, 5 pages.
Notice of Acceptance for Australian App. No. 2016350820 dated Jun. 5, 2020, 3 pages.
Notice of Reasons for Refusal for Japanese App. No. 2018-521194 dated Jun. 30, 2020, 27 pages.
Office Action dated Aug. 3, 2020 for U.S. Appl. No. 15/442,867 (pp. 1-10).
Office Action dated Jun. 11, 2020 for U.S. Appl. No. 15/431,073, (pp. 1-18).
Second Chinese Office Action for Chinese App. No. 201680077856.6 dated Jul. 21, 2020, 23 pages.
European Communication pursuant to Art. 94(3) for EP16824959.7 dated Jun. 3, 2020, 11 pages.
Brazilian Preliminary Examination Report for Brazilian Patent App. No. BR112018000507-0 dated May 12, 2020, 4 pages, (no English Translation).
Chinese Office Action for Chinese App. No. 201680047601.5 dated May 27, 2020, 8 pages.
Chinese Office Action for Chinese Patent App. No. 2019100617856 dated Feb. 5, 2021, 13 pages.
Giles et al., "Extrusion: The Definitive Processing Guide and Handbook" 2005, 517 pages.
Ren et al., "Different Dependence of Tear Strenth on Film Orientation of LLDPE Made with Different Co-Monomer" Polymers 2019, 11, 434, 13 pages.
Preliminary Notice of Patent Revocation for Korean Patent No. 10-2108157 dated Jan. 28, 2021, 13 pages.
Israeli Office Action for Israeli App. No. 256811 dated Jan. 25, 2021, 10 pages.
International Search Report and Written Opinion from corresponding PCT application dated Oct. 2, 2015 (15 pages).

* cited by examiner

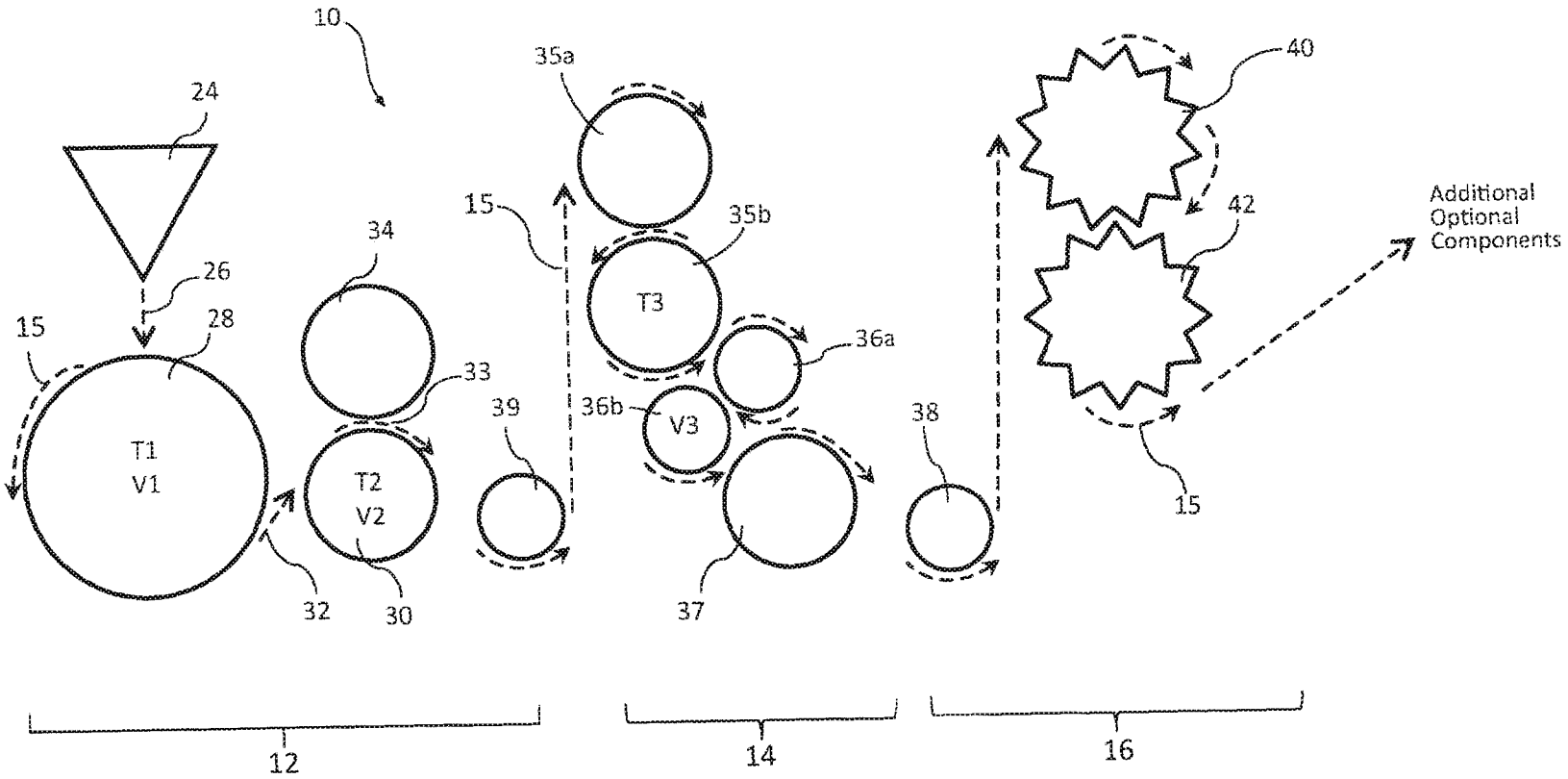
Additional Optional Components
40
42
15
16
38
36a
35b
T3
V3
36b
37
14
35a
15
39
33
34
T2
V2
30
10
32
12
24
26
28
T1
V1
15

BREATHABLE AND MICROPOROUS THIN THERMOPLASTIC FILM

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS

This application claims the benefit of priority of U.S. Provisional Patent Application No. 61/992,438, filed May 13, 2014, of U.S. Provisional Patent Application No. 62/053,385, filed on Sep. 22, 2014, and of U.S. Provisional Patent Application No. 62/092,351, filed Dec. 16, 2014, the disclosures of which are each hereby incorporated by reference.

FIELD OF THE INVENTION

The present invention relates to thin thermoplastic films, which have limited machine direction orientation (MDO) and desirable properties such as lack of holes, good breathability, and good tensile and tear strengths.

BACKGROUND

Thermoplastic films are widely used in personal care items, for example, as the outer layer of a diaper or other disposable personal hygiene product. For a variety of reasons, including cost, comfort, conservation of resources and minimizing waste, it is desirable to have as thin a film as possible while maintaining other necessary properties of the film.

Desirable qualities of thermoplastic films include being liquid impervious, vapor permeable (e.g., breathable), bondable to other layers of the personal care item, and having sufficient physical strength to be processed into a finished article. Strength is an important consideration when using thermoplastic films for packaging, for example, as an outer packaging for consumer goods. Breathable films having a sufficient strength and basis weight may be particularly useful as packaging for products that need to release odors resulting from the manufacturing process.

Thermoplastic films may be formed by extruding a molten polymeric composition onto a chill roller, where it is immediately cooled to make a solid film Processing of the film includes a variety of steps, including heating, cooling and stretching to produce a final film product having a thickness of 72 times or less than the initial thickness. Stretching in the machine direction (MD) forms a highly oriented thin gauge film, which is referred to as machine direction orientation (MDO). MDO may be useful, however, may also result in qualities such as reduced cross-directional (CD) tensile strength, impact strength, tear strength and slow puncture resistance, particularly in thinner films.

Current methods for making thin gauge thermoplastic films include those described in U.S. Pat. No. 7,442,332 (Cancio et al). In this process, a large part of the stretching (over half) of the web occurs between the extruder die and a first nip (i.e., in the "melt curtain"). In such a cast process, two drawbacks are the phenomenon known as "draw resonance," which results in uneven film thickness, and the formation of holes in the film. These problems increase with production speed, and furthermore may limit the types of polymeric compositions that can be used. Overcoming these issues requires slowing production, which ultimately results in increased cost.

A need exists, therefore, for thin thermoplastic films, which have limited MDO and desirable properties such as lack of holes, good breathability, good tensile strength and tear strength properties, and which can be produced economically and efficiently on high-speed production lines.

SUMMARY OF THE INVENTION

The present invention meets the aforementioned needs by providing breathable thermoplastic films having a low basis weight, that are substantially free of holes, and that have physical properties characteristic of films having a much higher basis weight. The films of the present invention exhibit excellent tensile strength, tear strength, and breathability. Whereas tear strength is proportional to the thickness of the film, with thicker films generally exhibiting higher tear strengths, the films made by the process of the present invention exhibit higher tear strengths than would be expected for comparative films of similar thickness. In other words, the films show an improved ratio of tear strength to thickness.

The thermoplastic films of the present invention, which are themselves believed to be unique, are made by a novel process in which the film is stretched in the MD at a temperature that is high enough to prevent detrimental MD orientation, yet below the melting point of the thermoplastic polymer. This process occurs downstream from a chilled roller, in contrast to the process described in U.S. Pat. No. 7,442,332. The method of the present invention allows the extrusion process to occur at normal production speeds, and without the need for additional equipment to reduce draw resonance. As an additional advantage, film qualities such as opacity may be controlled by additional downstream MD stretching, which reduces or eliminates the need to add opacifiers.

The following describe some non-limiting embodiments of the present invention. In one embodiment, a breathable, thermoplastic film is provided, which has a basis weight less than or equal to about 15 gsm and a water vapor transmission rate (WVTR) of at least about 500 grams $H_2O$/24-hour/$m^2$ and wherein said film has a ratio of the MD load at break to the CD load at break of less than about 10, and at least one of a machine-direction notched Elmendorf tear strength of at least about 5 g or a machine-direction notched trapezoidal tear strength of at least about 15 g.

In another embodiment, a laminate is provided, comprising a first layer which in turn comprises a breathable, thermoplastic film having a basis weight less than or equal to 15 gsm and a water vapor transmission rate of at least about 500 grams $H_2O$/24-hour/$m^2$, and wherein said film has a ratio of the MD load at break to the CD load at break of less than about 10, and at least one of a machine-direction notched Elmendorf tear strength of at least about 5 g or a machine-direction notched trapezoidal tear strength of at least about 15 g, said first layer having a surface; and a substrate attached to the surface of the film.

In another embodiment, a method of making a thermoplastic film product is provided, comprising extruding a molten web comprising a thermoplastic polymer from an extruder onto a first chill roller, said first chill roller operating at a peripheral velocity V1 and at a temperature T1, which is below the melting point of the thermoplastic polymer and which cools said web to form a film, and wherein a space between said extruder and chill roller forms a first gap; advancing the film to a stretching roller downstream from said first chill roller, which operates at a peripheral velocity V2 which is greater than V1, and at a temperature T2, and further stretching the film in the machine direction, to produce a film having a substantially uniform thickness and limited machine direction orientation, a ratio of the MD load at break to the CD load at break of less than about 10, and at least one of a machine-direction notched Elmendorf tear strength of at least about 5 g or a machine-direction notched trapezoidal tear strength of at least about 15 g.

In another embodiment is provided the above method, wherein the thermoplastic film has an MD load at break of at least 2.0 N/cm and a CD load at break of at least 0.7 N/cm.

In another embodiment is provided the above method, wherein the thickness of the thermoplastic film product is from about 5 gsm to about 20 gsm.

In another embodiment is provided the above method, wherein the molten web is cast, blown, calendered, mono-extruded, co-extruded, chill cast, nip embossed, or combinations thereof.

In another embodiment is provided the above method, further comprising at least one additional chill roller operating at a temperature T and a peripheral velocity V.

In another embodiment is provided the above method, further comprising the step of stretching the film in the cross-direction to produce a breathable thermoplastic film product having a water vapor transmission rate of at least about 500 grams—$H_2O$/24-hour/$m^2$.

In another embodiment is provided the above method, wherein the film is incrementally stretched in the cross-direction using interdigitated rollers.

In another embodiment is provided the above method, wherein the film is advanced through a first machine direction orientation section comprising at least one heated roller having a temperature T3 and at least one stretching roller.

In another embodiment is provided the above method, wherein the film is advanced through at least a second machine direction orientation section comprising at least one heated roller and at least one stretching roller.

In another embodiment is provided the above method, wherein said second machine direction orientation section is located downstream from a cross direction interdigitated roller section.

In another embodiment is provided the above method, wherein said second machine direction orientation section is located upstream from a cross direction interdigitated roller section.

In another embodiment is provided the above method, wherein T1 is from about 80° C. to about 160° C.

In another embodiment is provided the above method, wherein T2 is from about 60° C. to about 100° C.

In another embodiment is provided the above method, wherein T3 is from about 80° C. to about 150° C.

In another embodiment is provided the above method, wherein T is the same as T1.

In another embodiment is provided the above method, wherein T is different than T1.

In another embodiment is provided the above method, wherein V is the same as V1.

In another embodiment is provided the above method, wherein V is different than V1.

In another embodiment is provided the above method, wherein the chill roller and the stretching roller form a second gap of from about 7.5 cm to about 30 cm.

In another embodiment is provided the above method, wherein the ratio of V2 to V1 is from about 2 to about 8.

In another embodiment is provided the above method, wherein the film is a co-extruded multi-layer film.

In another embodiment is provided the above method, wherein the film is a mono-extruded film.

In another embodiment is provided the above method, wherein the film is a blown film.

In another embodiment is provided the above method, wherein the film has an opacity of at least about 50%.

In another embodiment is provided the above method, wherein said film comprises an olefin block copolymer is ethylene-based, propylene-based, or combinations thereof.

In yet another embodiment, a breathable, thermoplastic film is provided, which is produced by a process wherein a molten web comprising a thermoplastic polymer is extruded onto a chill roller having a temperature T1 to form a film, the film is advanced to a stretching roller having temperature T2 downstream from said first chill roller, and further advanced through a first machine direction orientation section comprising at least one heated roller having a temperature T3 and at least one stretching roller, wherein limited machine direction orientation is imparted to the film, and wherein the film has a basis weight less than or equal to about 15 gsm, a water vapor transmission rate of at least about 500 grams $H_2O$/24-hour/$m^2$, and wherein said film has a ratio of the MD load at break to the CD load at break of less than about 10.

In another embodiment is provided the film produced by the above process, wherein the film has an Elmendorf tear strength in the machine direction of at least 5 g.

In another embodiment is provided the film produced by the above process, wherein the film has a trapezoidal tear strength in the machine direction of at least 15 g.

In another embodiment is provided the film produced by the above process, wherein the film has an MD load at break of at least 2.0 N/cm and a CD load at break of at least 0.7 N/cm.

In another embodiment is provided the above film produced by the above process, wherein the molten web is cast, blown, calendered, mono-extruded, co-extruded, chill cast, nip embossed, or combinations thereof.

In another embodiment is provided the film produced by the above process, wherein the film is a coextruded multi-layer film.

In another embodiment is provided the film produced by the above process, wherein the film is a monolayer film.

In another embodiment is provided the film produced by the above process, wherein the film has a hydrohead pressure of at least 200 psi.

In another embodiment is provided the film produced by the above process, wherein the film is incrementally stretched in the cross-direction using interdigitated rollers.

In another embodiment is provided the film produced by the above process, wherein the film has an opacity of at least about 50%.

BRIEF DESCRIPTION OF THE DRAWINGS

The FIGURE depicts one non-limiting embodiment of an apparatus suitable for making the films of the present invention.

DETAILED DESCRIPTION OF THE INVENTION

As used herein:

"Activation defect," "activation holes," or "pinholes," mean small holes or tears in a film while the film undergoes formation, lamination, activation, or other manufacturing or processing steps, which in turn may lead to reduced tear strength, increased porosity, increased leakage or other undesirable characteristics.

"Gsm" means grams per square meter, and is a measure of the basis weight, which is an industry standard term that quantifies the thickness or unit mass of a film or laminate product.

"Hydrohead pressure" is may be measured according to method AATCC 127-2008, and may be expressed in units of pounds per square inch, or psi. The films of the present invention have a hydrohead pressure of at least 200 psi.

"Skin layer(s)" means one or both outer layers of a multilayer film that function as an outer surface of the film.

"Tear strength" or "tear force," reflects the ease or difficulty by which the film can be torn, and is expressed in units of grams. Herein, tear strength may be measured by the Elmendorf notched tear test, ASTM D-1922, incorporated herein by reference and/or by the Trapezoid tear test ("trap test"), as described herein or according to ASTM D-5587. The test may be performed with either a notched or an unnotched film and in either the CD or MD direction. Unless otherwise specified, herein tear strength is notched tear strength. It is noted that tear strength is related to film thickness, and any comparison of tear strengths must take into account the relative basis weights of the comparative samples.

"Tensile strength," means the load required to induce a break ("load at break") in the film in either the CD or the MD. Tensile strength is expressed in units of N/cm or equivalent units thereof, and is determined by ASTM method D822-02, using the following parameters: Sample Direction=MD×CD; Sample size=1 inch width×6 inch length; Test speed=20 inimin; Grip distance=2 inch. Grip size=3 inch wide rubber faced grips evenly gripping sample.

"WVTR" means "water vapor transmission rate," and is a measure of film breathability. WVTR is expressed in units of g $H_2O$/24 hours/$m^2$ or equivalent units thereof, and may be measured according to ASTM method D-6701-01.

Film

The films of the present invention are thermoplastic monolayer or multilayer films and may have a basis weight of from about 5 gsm to about 20 gsm, alternatively from about 5 to about 15 gsm, alternatively from about 10 to about 15 gsm, alternatively from about 8 to about 13 gsm, alternatively from about 10 gsm to about 12 gsm, alternatively less than about 15 gsm, alternately less than 14 gsm, alternatively less than about 12 gsm, and alternatively less than about 10 gsm. Multilayer films of the present invention may comprise at least 2 layers, alternatively at least 3 layers, alternatively at least 5 layers, alternatively at least 7 layers, alternatively at least 9 layers, alternatively at least 11 layers, alternatively from 2 to about 20 layers, alternatively from 3 to about 11 layers, and alternatively from 5 to 11 layers. The films may or may not comprise a skin layer to reduce tackiness of one or both external surfaces.

The films of the present invention have a CD load at break greater than 0.7 N/cm, alternatively greater than about 0.8 N/cm, alternatively greater than about 0.9 N/cm, alternatively from about 0.7 N/cm to about 3.0 N/cm, and alternatively from about 0.7 N/cm to about 2.0. The films of the present invention have an MD load at break of at least about 2.0 N/cm, alternatively of at least about 2.5 N/cm, alternatively at least about 3.0 N/cm, alternatively from about 2.0 N/cm to about 6.0 N/cm and alternatively from about 3.0 N/cm to about 6.0 N/cm.

An important and inventive aspect of the present invention, however, is the ratio of the MD to the CD load at break, which is a measure of an improved balance between these properties and which is not present in previously disclosed films. Without wishing to be limited by theory, it is believed that this advantageous ratio is achieved by reducing machine direction orientation in the films by the process disclosed herein. The films of the present invention have a ratio of MD load at break to CD load at break of from about 1 to about 15, alternatively from about 1 to about 10, alternatively from about 1 to about 9, alternatively from about 1 to about 8, alternatively from about 1 to about 5, alternatively of less than about 10, alternatively less than about 9, alternatively less than about 8, alternatively less than about 5, alternatively less than about 4, and alternatively of about 1.

The films of the present invention further have a water vapor transmission rate (WVTR) of at least 500 grams $H_2O$/24-hour/$m^2$, alternatively at least 1,000 grams $H_2O$/24-hour/$m^2$, alternatively at least 2,000 grams $H_2O$/24-hour/$m^2$ alternatively at least 3500 grams $H_2O$/24-hour/$m^2$, alternatively of at least 4500 grams $H_2O$/24-hour/$m^2$, alternatively of at least about 6,000 grams $H_2O$/24-hour/$m^2$, alternatively of at least about 7,000 grams $H_2O$/24-hour/$m^2$, alternatively of at least about 9,000 grams $H_2O$/24-hour/$m^2$, and alternatively of from about 1,000 grams $H_2O$/24-hour/$m^2$ to about 10,000 grams $H_2O$/24-hour/$m^2$.

The films of the present invention further have an Elmendorf tear strength in the machine direction of at least about 5 g, alternatively of at least about 10 g, alternatively of at least about 15 g, alternatively from about 5 g to about 50 g, alternatively from about 10 g to about 45 g, and alternatively from about 15 g to about 45 g.

The films of the present invention further have a trapezoidal ("trap") tear strength in the machine direction of at least about 15 g, alternatively of at least about 20 g, alternatively of at least about 25 g. alternatively from about 15 g to about 150 g, alternatively from about 15 g to about 100 g, and alternatively from about 15 g to about 85 g.

The films of the present invention comprise one or more thermoplastic polymers. Suitable polymers for the films include, but are not limited to, polyolefins, for example, polyethylene homopolymers and copolymers, polypropylene, polypropylene homopolymers and copolymers, functionalized polyolefins, polyesters, poly(ester-ether), polyamides, including nylons, poly(ether-amide), polyether sulfones, fluoropolymers, polyurethanes, and mixtures thereof. Polyethylene homopolymers include those of low, medium or high density and/or those formed by high pressure or low pressure polymerization. Polyethylene and polypropylene copolymers include, but are not limited to, copolymers with C4-C8 alpha-olefin monomers, including 1-octene, 1-butene, 1-hexene and 4-methyl pentene. The polyethylene may be substantially linear or branched, and may be formed by various processes known in the art using catalysts such as Ziegler-Natta catalysts, metallocene or single-site catalysts or others widely known in the art. Examples of suitable copolymers include, but are not limited to, copolymers such as poly(ethylene-butene), poly(ethylene-hexene), poly(ethylene-octene), and poly(ethylene-propylene), poly(ethylene-vinylacetate), poly(ethylene-methylacrylate), poly(ethylene-acrylic acid), poly(ethylene-butylacrylate), poly(ethylene-propylenediene), poly(methyl methacrylate) and/or polyolefin terpolymers thereof. In one embodiment, the films comprise polyethylene, polypropylene, and combinations thereof. One example of a suitable commercially available polyethylene-based resin is Exceed™ 3527PA made by Exxon. One example of a suitable commercially available polypropylene copolymer is Borealis BD712 made by Borealis.

Other non-limiting examples of suitable olefinic polymeric compositions include olefinic block copolymers, olefinic random copolymers, polyurethanes, rubbers, vinyl arylenes and conjugated dienes, polyesters, polyamides, polyethers, polyisoprenes, polyneoprenes, copolymers of any of the above, and mixtures thereof. In addition, the films of the present invention, or layers thereof, may comprise brittle polymers, nonlimiting examples of which are disclosed in U.S. Pat. No, 7,879,452. In one embodiment, the films comprise an olefinic block copolymer.

In one embodiment, the olefinic block copolymer is polypropylene-based. Non-limiting examples of suitable polypropylene-based olefinic block copolymers are sold under the trade name INFUSE™ by The Dow Chemical Company of Midland, Mich., the trade name VISTAMAXX® by ExxonMobil Chemical Company of Houston, Tex., and the trade name Exxon Impact® Copolymers such as Exxon PD 7623. Polypropylene, as well as polyesters, is both known to increase the melting temperature of a formed polymeric film, improving the film's burn through resistance. In an alternative embodiment, the films of the present invention may comprise an ethylene-based olefinic block copolymer.

The aforementioned thermoplastic polymers may be present in the film or in individual layers of the film in an amount of from 0% to about 95%, alternatively from about 0% to about 40%, alternatively from about 10% to about 50%, alternatively from about 35% to about 50%, alternatively from about 20% to about 40%, and alternatively from about 1% to about 10%.

In one embodiment, the film, or one or more layers of a multilayer film, comprises from about 0.1% to about 90%, alternatively from about 1% to about 60%, alternatively from about 20% to about 50%, alternatively from about 20% to about 40%, an alternatively from about 1% to about 10% of polypropylene, a polypropylene-based composition or copolymer, ethylene, an ethylene-based composition or copolymer, or combinations thereof.

The films of the present invention, or individual layers thereof, may comprise one or more elastomeric polymers, including styrenic block copolymers, elastomeric olefinic block copolymers and combinations thereof. Non-limiting examples of suitable styrenic block copolymers (SBC's) include styrene-butadiene-styrene (SBS), styrene-isoprene-styrene (SIS), styrene-ethylene-butylene-styrene (SEBS), styrene-ethylene-propylene (SEP), styrene-ethylene-propylene-styrene (SEPS), or styrene-ethylene-ethylene-propylene-styrene (SEEPS) block copolymer elastomers, polystyrene, and mixtures thereof. In one embodiment, the film comprises styrene-butadiene-styrene, polystyrene, and mixtures thereof. Suitable SBC resins are readily available from: KRATON® Polymers of Houston, Tex.; Dexco™ Polymers LP of Planquemine, LA; or Septon™ Company of America of Pasadena, Tex.

The films of the present invention may include optional components, such as fillers, such as calcium carbonate, plasticizers, compatibilizers, draw down polymers, processing aids, anti-blocking agents, viscosity-reducing polymers, and the like. Other additives may include pigments, dyes, antioxidants, antistatic agents, slip agents, foaming agents, heat or light stabilizers, UV stabilizers, and the like. Examples of suitable processing aids and anti-blocking agents include, but are not limited to, Ampacet™, available from Ampacet Corporation. In one embodiment, the polymeric compositions may comprise from about 0% to about 75%, alternatively 1% to 30% and alternatively from about 30% to about 60%, of filler. In one embodiment, the polymeric compositions may comprise from about 0% to about 15%, and alternatively from about 0% to about 10%, and alternatively from about 0.5% to about 5%, of a suitable processing aid.

In one embodiment, the films are substantially free of titanium dioxide, and alternatively comprise less than 0.1% titanium dioxide. The films may have an opacity greater than 50%, alternatively greater than 55%, and alternatively greater than about 60%.

Apparatus

The Figure depicts exemplary designs of a film forming apparatus 10 which are suitable for forming the films of the present invention. "Machine direction" as applied to a film or nonwoven material, means the direction that is parallel to the direction of travel of the film or nonwoven as it is processed in the film forming apparatus. The "cross direction" means the direction perpendicular to the machine direction. In one nonlimiting embodiment, and as depicted in the Figure, film forming apparatus 10 comprises a casting/drawing section 12, a machine direction orientation (MDO) section 14, and a cross direction interdigitated roller (CDI) section 16. Optionally, film forming apparatus 10 may comprise additional sections as would be apparent to one of skill in the art, such as an annealer section, a winder, an additional machine direction orientation section, and/or a corona treatment section, In other embodiments, the order of the sections or components thereof may differ than those depicted in the Figure, as also would be understood by one of skill in the art.

The casting/drawing section 12 comprises an extruder 24 followed by at least one chill roller 28 with a first gap 26 therebetween. As would be understood by one of skill in the art, the position of extruder 24 relative to chill roller 28 may vary from that shown in the Figure to a position slightly more downstream from that shown, yet in which the extruder 24 is still in a position to deposit a melt curtain comprising the extrudate onto the chill roller 28. Downstream of the chill roller 28, which has a temperature T1 and rotates at a speed V1, is a stretching roller 30, having a temperature T2 and rotating at a speed V2. The chill roller 28 is separated from the stretching roller 30 by a second gap 32. In operation, the extruder 24 melts and extrudes an extrudate across gap 26 onto chill roller 28, forming a web, or film, 15. Film 15 travels across second gap 32 into the nip 33 formed between slave roller 34 and stretching roller 30. The film 15 then passes over an idle roller 39 to the machine direction orientation section 14.

The webs, or films, of the present invention may be formed by a variety of means that would be understood by skill in the art, and may be cast, blown, calendered, mono-extruded, co-extruded, chill cast, nip embossed, or any other method which would result in a film compatible with the process described herein.

In one embodiment, the thermoplastic polymeric film formulation may be blended in the extruder 24, for example at a temperature of from about 210° C. to about 280° C. The exact temperature will depend upon the formulation of the polymeric compositions. The web, or "melt curtain," comprising the polymeric composition may be extruded (or coextruded if a multilayer film is being formed) onto the chill roller 28. The temperature T1 of the chill roller 28 is carefully controlled so that the film 15, as it leaves the chill roller 28, is at a temperature sufficiently high that it can be stretched to the desired thickness without significant MD molecular orientation, yet below the melting temperature of the polymeric composition. Thus, the temperatures T1 and T2 are dependent upon the composition of the film. T1 may be greater than 80° C., alternatively from about 80° C. to about 160° C., alternatively is 90° C. to about 160° C., alternatively is from about 100° C. to about 140° C., alternatively from about 80° C. to about 120° C., alternatively from about 100° C. to about 120° C., and alternatively less than about 160° C. The temperature, T2, of stretching roller 30, may be greater than 40° C., alternatively from about 40° C. to about 100° C., alternatively from about 60° C. to about 100° C., alternatively from about 60° C. to about 90° C., alternatively from about 85° C. to about 90° C., and alternatively less than about 100° C.

It is noted that in the present invention, the temperature T1 of chill roller 28 and the temperature T2 of stretching roller 30, are significantly higher than in any previously disclosed MDO process. In previous applications, T1 typically is from about 10° C. to about 60° C., and T2 typically is from about 10° C. to about 40° C. The present invention utilizes a temperature which balances the need for film processability and yet which allows for controlling the amount of MDO.

In one embodiment, at least two chill rollers are present, each having a speed V and a temperature T. The speeds and temperatures of the chill rollers each may be the same or different, however will be sufficient for the film to be stretched to the desired thickness without significant MD molecular orientation, yet below the melting temperature of the polymeric composition. By way of nonlimiting example only, the temperatures may differ by 5° C., by 10° C., or greater. The chill rollers may each individually be smooth, textured, coated (e.g., with a release treatment), which may be the same or different on each roll.

The length of first gap 26 between the extruder 24 and chill roller 28 is the shortest distance between the extruder 24 and the chill roller 28, and is greater than previous cast MDO processes. In one embodiment, the length of the first gap 26 is greater than 2.5 cm, alternatively is from about 2.5 cm to about 25 cm, alternatively from about 3 cm to about 15 cm, and alternatively is from about 3 cm to about 7.6 cm. The extrudate may undergo a melt curtain stretch, with a corresponding reduction in thickness, in gap 26 of from 10 times to about 25 times (about 10× to about 25×).

In one embodiment, the apparatus may include an additional roller and a nip between the extruder 24 and the chill roller 28, as depicted in U.S. Pat. No. 7,442,332. In another embodiment, the apparatus may include one or more additional chill rollers. In yet another embodiment, chill roller 28 may be replaced by two rollers, wherein the rollers form an additional nip. The rollers may be a metal roller and a rubber roller, and the metal roller optionally may be embossed. The temperature of the film in the nip is about 120° C. or below, and alternatively about 100° C. or below. After passing through the additional nip, the film is advanced through nip 33 and further through the process described herein.

The ratio of the velocities of the rolls V2/V1 provides the relative length a film is stretched.. Thus, a ratio 1/1 (1×) indicates the film has not been stretched. A ratio of 5/1 (5×) indicates a film has been stretched 5 times its length before stretching with a corresponding reduction in film thickness, i.e. 0.2 times its thickness prior to stretching. In one embodiment, the ratio of V2/V1 is at least 2, alternatively is at least 5, alternatively is from about 2 to about 8, alternatively is from about 3 to about 8, and alternatively is less than 5.

The length of the second gap 32 between the chill roller 28 and the nip 33 at the stretching roller 30 is the shortest distance between the chill roller 28 and the stretching roller 30, and in one embodiment is at least about 7.5 cm, alternatively is from about 7.5 to about 30 cm, alternatively is from about 7.5 to about 20 cm, alternatively is from about 7.5 cm to about 10 cm, alternatively is about 30 cm, alternatively is about 20 cm, alternatively is about 15 cm, alternatively is about 15 cm, and alternatively is less than 10 cm. The film 15, after being stretched between chill roller 28 and stretching roller 30, is essentially a nonporous film having limited molecular orientation in the MD.

Herein, "imparting limited machine direction orientation to the film" means to produce sufficient MD orientation to give the film an MD load at break of at least 2.0 N/cm with a CD load at break of at least 0.7 N/cm. In addition, the film will have a ratio of MD load at break to CD load at break of from about 1 to about 15. Although the amount of MDO may not be directly quantifiable, the amount of MDO correlates to the properties of the film. A film that has limited MDO will have, in particular, improved CD properties, such as CD Elmendorf and Trapezoidal tear strength, CD tensile strength at break, and an improved balance of CD and MD tensile strengths relative to previously described films.

Downstream from casting/drawing section 12, the film 15 may pass from stretching roller 30 around idle roller 39 to a first machine direction orientation (MDO) section 14. The purpose of this section is to further stretch the film in the machine direction while still avoiding significant MD orientation. MDO section 14 may include heated rollers 35a and 35b, followed by stretching rollers 36a and 36b and/or cooling roller 37. At heated rollers 35a-35b, filter 15 is heated to a temperature T3. T3 will depend on the composition of the film, and will be sufficient to avoid significant MD orientation. In one embodiment, T3 is from about 80° C. to about 150° C., alternatively is greater than 95° C. and alternatively is greater than 120° C.

As would be understood by one of skill in the art, the number of stretching rollers, heated rollers and chill rollers within first MDO section 14 may vary, as well as the number of MDO sections. Thus, in an alternative embodiment, the apparatus may comprise one or more additional sets of stretching rollers, heated rollers, and/or cooling rollers to impart desired physical and aesthetic characteristics, such as porosity and opacity. By way of example, a second set of heated rollers, stretching rollers and/or cooling roller may be located in first MDO section 14, downstream from stretching rollers 36a and 36b and upstream from cooling roller 37. In an alternative embodiment, a second set of heated rollers, stretching rollers and/or cooling roller are located downstream from CDI section 16 in a second MDO section.

The film 15 moves downstream from MDO section 14 at a speed of V3. In one embodiment, the ratio of V3/V1 is greater than 1, alternatively greater than 2, alternatively less than 25, alternatively from about 2 to about 25, alternatively from about 5 to about 15, alternatively from about 5 to about 25. In one embodiment, the ratio of V3/V2 and/or of V2/V1 is greater than 1, alternatively is greater than 2, alternatively is less than 5, alternatively is from about 1 to about 5, and alternatively is from about 2 to about 5.

Cross direction interdigitated roller (CDI) section 16, if present, may include a tensioning roller 38 followed by interdigitating rollers 40, 42. In the present invention, interdigitating rollers 40, 42 are designed to stretch the film in the cross direction, resulting in additional film activation and imparting breathability. In one embodiment, machine direction into rollers are used in place in of, or in addition to, cross direction interdigitating rollers 40, 42, either before or after CDI section 16. Suitable cross direction interdigitated rollers are described in U.S. Pat. No. 7,442,332.

In place of MDO section and or CDI section or in addition to these sections, the film can be stretched using a tentering frame (not shown). This can be used to effect both MDO and CDO.

The film 15 may move from the CDI section 16 to other optional components, including but not limited to, a corona treatment section, an annealing, section, a second MDO section and/or a winder, where it is then ready for its intended use. The films of the present invention are useful for a variety of purposes, including, for example, use in personal hygiene products relating such as disposable absorbent products. Non-limiting examples include diapers, training pants, adult incontinence pads and pants, swimwear, sanitary napkins, tampons, pantiliners, etc. In one embodiment, the present invention is related to an absorbent article comprising the films described herein. In one embodiment, the absorbent article is a diaper.

The present invention further describes laminates comprising the films of the present invention. The laminates comprise a first layer comprising the breathable, thermoplastic films described herein, and a substrate attached to one or both surfaces of the film. The substrate may be any woven or a nonwoven material suitable for use with thermoplastic films, and in one embodiment is a spunbond nonwoven. The substrate may have a basis weight of 100 gsm or less, alternatively 50 gsm or less, alternatively 25 gsm or less, alternatively 15 gsm or less, and alternatively 10 gsm or less. The substrate may be attached to the film by a variety of means such as adhesive lamination, ultrasonic bonding, extrusion bonding, etc.

The films and/or laminates of the present invention are suitable for use as diaper backsheets or ears (closure tabs), and may be formed into pouches for packaging, wrapping products such as personal hygiene items, as well as foods such as sandwiches, fruits, vegetables and the like, breathable poly bags such as breathable diaper poly bags. Other non-limiting examples of articles in which the laminates of the present invention may be used include building applications, such as roofing and wall linings, and backsheets for flooring and carpeting.

The invention will be further appreciated in light of the following detailed examples, Opacity The opacity of the film is measured as follows: The method uses the ratio of the reflectance of the sample combined with a white backing, to the same sample combined with a black backing. A Hunterlab colorimeter D25A is calibrated and standardized according to manufacturer's specifications. Samples are cut large enough to cover the meter's porthole opening. The sample is placed on the port with the rubber roll side or curl side up. The sample is covered with an uncalibrated white tile. "Read" and "xyz" are pressed. The white tile is removed. The sample is covered with black glass tile. 100% is pressed. The "y" value of the sample will be displayed, along with the opacity value in percent. In all examples, the samples were subjected to CD incremental stretching (CDI).

Alternatively, film opacity may be measured according to ASTM D1746.

Hydrohead Pressure

The hydrohead pressure may be measured according to the method described in AATCC 127-2008. Specifically, a Textest Instrument FX 3000 Hydrotester III, 05/07 s/n 597 or higher may be used. The standard test gradient is 60 mbar/min, and a 70 gsm spunbond/pattern bond polypropylene nonwoven is used as a support. The test endpoint is the third drop, and the pressure in mbar is recorded when the first, second and third drops penetrate the sample and/or the pressure when the sample bursts. If no water penetration is observed, the maximum test pressure is recorded.

Trap Tear Strength

A sample template is cut having dimensions 3"×6". From this template, mark a trapezoidal template having a long side of 4", a parallel short side of 1", and a height (distance between the parallel sides, measured perpendicularly to the sides) of 3". Beginning at the middle of the edge of the short side, cut a slit perpendicular to the short side having a length of ⅝". Place template in clamps of an Instron Model 1122, 4301 or equivalent tensile testing unit having a constant rate of extension. The distance between the clamps is set to 1". Adjust and standardize the load cell according to the instructions. For Tensile Testers equipped with Series IX software, select appropriate Series IX test method from the "method" menu in the software.

Set the load range of the testing unit so that maximum load occurs at 85% of full-scale load. Set the crosshead travel at twelve inches (12") per minute. Secure the template in the upper and lower clamps along the marked, non-parallel side of the trapezoid so that one end edge of the clamps is in line with the one inch (1") side of the trapezoid and the cut is halfway between the clamps. Start the test unit and record the tearing force of the specimens.

Example 1:

A film was formed according to the previously-described method. The polymeric formulation by weight included 48% polyethylene, 45% calcium carbonate, 6% polypropylene and 1% processing aids. This formulation was melt blended and extruded as a monolayer at a temperature at about 260° C. and extruded onto a chill roller rotating at approximately 45.7 meters per minute and a temperature of 116° C. The film was stretched at a stretching roller operating at a velocity V2 of 149 meters per minute and a temperature of 88° C. It was then stretched at an MDO operating at a speed of 278 meters per minute and a temperature of less than 95° C. The formed film had a basis weight of 11.4 gsm and a CD load at break of 1.14 Newtons/cm. The cross direction elongation at break was 446%. In the machine direction, the load at break was 3.16 Newtons/cm. The machine direction elongation at break was 269%. The opacity was 59.4%, and no $TiO_2$ was added. The water vapor transmission rate (WVTR) was 9,083 grams $H_2O$/24 hours/$m^2$. These data points all exceed the specifications for a 16 gsm basis weight film with a reduction in materials.

Examples 2 Through 11:

Using the method disclosed in Example 1, additional cast films were formed. The samples contained 1% processing aids, polypropylene and fillers as noted below, with the remainder of the composition comprising polyethylene. The physical characteristics of the films are shown in the Table 1. Unless otherwise noted, the films comprised 50% calcium carbonate and did not contain titanium dioxide.

According to Example 2, a three layer film was formed, wherein the skin layers comprised polyethylene with 4% polypropylene and the core layer comprised polyethylene with 33% polypropylene. The percentage of the thickness of the layers A/B/A was 15/70/15.

In Example 3, a monolayer film is formed comprising polyethylene, 11% polypropylene and 47% calcium carbonate filler.

In Example 4, a monolayer film was formed comprising 9% polypropylene. The ratio of V2/V1 was 2.2 and the ratio of V3/V2 is 2.0.

In Example 5, a monolayer film was formed comprising 16% polypropylene. The ratio of V2/V1 was 3.2 and the ratio of V3/V2 is 2.5.

In Examples 6 and 7, monolayer films were formed comprising 33% polypropylene. The ratio of V2/V1 was 4.0 and 3.5 respectively and the ratio of V3/V2 was 1.5 and 1.3 respectively.

In Example 8, a multilayer film comprising three layers was formed, in which the outer layers comprised 0% polypropylene and the inner layer comprised 33% polypropylene. The ratio of V2/V1 was 3.2 and V3/V2 is 2.0. The percentage of the thickness of the layers A/B/A was 15/70/15.

In Examples 9 and 10, a monolayer film comprising 33% polypropylene was formed as well as a rubber additive. The ratio of V2/V1 was 3.5 V3/V2 for example 9 is 1.3 and for example 10 is 1.5.

In Example 11, a monolayer film is formed, comprising 21% polypropylene and 46% calcium carbonate. The ratio of V2/V1 is 3 and the ratio of V3/V2 is 2.

TABLE 1

| Sample | Basis Weight (gsm) | MD Load at Break (N/cm) | CD Load at Break (N/cm) | MD Elmendorf Tear Strength (g) | MD Trapezoidal Tear Strength (g) | Opacity (%) | WVTR (grams $H_2O$/24-hour/$m^2$) | Hydro Head Pressure (psi) |
|---|---|---|---|---|---|---|---|---|
| 2 | 12.6 | 4.8 | 1.4 | | | 62 | 7938 | 444 |
| 3 | 9.7 | 3.6 | 0.9 | | | 51 | 6571 | 430 |
| 4 | 11.4 | 3.2 | 1.1 | 15 | 82 | 59 | 9083 | |
| 5 | 11.5 | 3.3 | 0.9 | 19 | 33 | 57 | 7527 | |
| 6 | 8.6 | 2.7 | 1.2 | 16 | 51 | 51 | 3320 | |
| 7 | 11.3 | 2.6 | 1.8 | 16 | 58 | 63 | 4660 | |
| 8 | 12.5 | 5.1 | 1.2 | 16 | 27 | 65 | 7487 | |
| 9 | 12.5 | 3.7 | 1.9 | 43 | 134 | 54 | 2810 | |
| 10 | 11.5 | 3.4 | 1.6 | 16 | 75 | 57 | 7487 | |
| 11 | 13.3 | 4.7 | 0.8 | 13 | | 45.9 | 1800 | |

In all embodiments of the present invention, all ranges are inclusive and combinable. All numerical amounts are understood to be modified by the word "about" unless otherwise specifically indicated. To the extent that the terms "includes," "including," "contains," or "containing" are used in the specification or the claims, they are intended to be inclusive in a manner similar to the term "comprising" as that term is interpreted when employed as a transitional word in a claim.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

Whereas particular embodiments of the present invention have been illustrated and described, it would be obvious to those skilled in the art that various other changes and modifications can be made without departing from the spirit and scope of the invention. It is therefore intended to cover in the present claims all such changes and modifications that are within the scope of this invention.

What is claimed is:

1. A breathable, thermoplastic film having a basis weight less than or equal to about 15 gsm and a water vapor transmission rate of at least about 500 grams $H_2O$/24-hour/$m^2$; wherein said film has a ratio of the MD load at break to the CD load at break of less than about 10, and at least one of a machine-direction notched Elmendorf tear strength of at least about 5 g or a machine-direction notched trapezoidal tear strength of at least about 15 g.

2. The film according to claim 1, wherein the MD load at break is at least about 2.0 N/cm and the CD load at break is at least about 0.7 N/cm.

3. The film according to claim 1 having an opacity of at least about 50%.

4. The film according to claim 3, wherein said film is substantially void of titanium dioxide.

5. The film according to claim 1, wherein said film comprises an olefin block copolymer.

6. The film according to claim 5, wherein the olefin block copolymer is a propylene-based polymeric composition.

7. The film according to claim 5, wherein the olefin block copolymer is an ethylene-based polymeric composition.

8. The film according to claim 1, wherein the film comprises from about 10% to about 60% of polypropylene.

9. The film according to claim 1 wherein said film comprises from about 30% to about 60% by weight of a filler.

10. The film according to claim 1, wherein the film is a coextruded multilayer film.

11. The film according to claim 1, wherein the film is a monolayer film.

12. The film according to claim 1, wherein the film has a hydrohead pressure of at least 200 psi.

13. A breathable, thermoplastic film having a basis weight of from about 5 gsm to about [20] *15* gsm; a water vapor transmission rate of at least about 500 grams [—] $H_2O$/24-hour/$m^2$; a CD load at break of at least 0.7 N/cm; an MD load at break of at least about 2.0 N/cm; a ratio of the MD load at break to the CD load at break of from about 1 to about 10, and at least one of a machine-direction notched Elmendorf tear strength of at least about 5 g or a machine-direction notched trapezoidal tear strength of at least about 15 g.

14. The film according to claim 13 having an opacity of at least about 50%.

15. The flint according to claim 13, wherein said film comprises an olefin block copolymer.

16. The film according to claim 15, wherein the olefin block copolymer is a propylene-based polymeric composition.

17. The film according to claim 13, wherein the film comprises from about 10% to about 60% of polypropylene.

18. The film according to claim 13 wherein said film comprises from about 30% to about 60% by weight of a filler.

19. The film according to claim 13, wherein the film is a coextruded multilayer film.

20. A laminated article comprising:

a. a first layer comprising a breathable, thermoplastic film having a basis weight less than or equal to about 15 gsm and a water vapor transmission rate of at least about 500 grams $H_2O$/24-hour/$m^2$; wherein said film has a ratio of the MD load at break to the CD load at break of less than about 10, and at least one of a machine-direction notched Elmendorf tear strength of at least about 5 g or a machine-direction notched trapezoidal tear strength of at least about 15 g, said first layer having a surface;

b. a substrate attached to the surface of the film.

* * * * *